(12) United States Patent
Jackson

(10) Patent No.: US 10,308,593 B2
(45) Date of Patent: Jun. 4, 2019

(54) ADDITIVES FOR FUEL OILS

(75) Inventor: Graham Jackson, Reading (GB)

(73) Assignee: INFINEUM INTERNATIONAL LIMITED, Abingdon, Oxfordshire (GB)

(*) Notice: Subject to any disclaimer, the term of this patent is extended or adjusted under 35 U.S.C. 154(b) by 443 days.

(21) Appl. No.: 12/634,796

(22) Filed: Dec. 10, 2009

(65) Prior Publication Data

US 2010/0236139 A1    Sep. 23, 2010

(30) Foreign Application Priority Data

Mar. 18, 2009   (EP) .................................... 09155478

(51) Int. Cl.
| | | |
|---|---|---|
| *C07C 229/12* | (2006.01) | |
| *C07C 237/08* | (2006.01) | |
| *C07C 229/24* | (2006.01) | |
| *C07C 237/06* | (2006.01) | |
| *C07C 237/10* | (2006.01) | |
| *C10L 1/14* | (2006.01) | |
| *C10L 1/22* | (2006.01) | |
| *C10L 1/222* | (2006.01) | |
| *C10L 1/224* | (2006.01) | |
| *C10L 10/00* | (2006.01) | |
| *C10L 10/14* | (2006.01) | |
| *C10L 10/18* | (2006.01) | |
| *C10L 1/16* | (2006.01) | |
| *C10L 1/19* | (2006.01) | |
| *C10L 1/197* | (2006.01) | |
| *C10L 1/198* | (2006.01) | |
| *C10L 1/223* | (2006.01) | |
| *C10L 1/2383* | (2006.01) | |

(52) U.S. Cl.
CPC .......... *C07C 237/08* (2013.01); *C07C 229/12* (2013.01); *C07C 229/24* (2013.01); *C07C 237/06* (2013.01); *C07C 237/10* (2013.01); *C10L 1/143* (2013.01); *C10L 1/221* (2013.01); *C10L 1/224* (2013.01); *C10L 1/2222* (2013.01); *C10L 10/00* (2013.01); *C10L 10/14* (2013.01); *C10L 10/18* (2013.01); *C10L 1/1658* (2013.01); *C10L 1/19* (2013.01); *C10L 1/1973* (2013.01); *C10L 1/1976* (2013.01); *C10L 1/1981* (2013.01); *C10L 1/223* (2013.01); *C10L 1/2225* (2013.01); *C10L 1/2383* (2013.01)

(58) Field of Classification Search
CPC .... C10L 1/238; C10L 1/00; C10L 1/18; C10L 2200/0259; C10L 1/224
USPC .......................................................... 44/394
See application file for complete search history.

(56) References Cited

U.S. PATENT DOCUMENTS

| | | | |
|---|---|---|---|
| 2,438,091 A | 3/1948 | Lynch | |
| 2,921,085 A * | 1/1960 | Schramm | .............. C07C 237/00 516/14 |
| 3,172,892 A | 3/1965 | Le Suer | |
| 3,219,666 A | 11/1965 | Norman | |
| 3,272,746 A | 9/1966 | Le Suer et al. | |
| 3,310,492 A | 3/1967 | Benoit | |
| 3,341,542 A | 9/1967 | Le Suer et al. | |
| 3,444,170 A | 5/1969 | Norman et al. | |
| 3,445,441 A * | 5/1969 | Rushton | .................... C02F 1/52 210/734 |
| 3,455,831 A | 7/1969 | Davis | |
| 3,455,832 A | 7/1969 | Davis | |
| 3,576,743 A | 4/1971 | Meinhardt et al. | |
| 3,630,904 A | 12/1971 | Friihauf et al. | |
| 3,632,511 A | 1/1972 | Liao | |
| 3,804,763 A | 4/1974 | Meinhardt | |
| 3,864,098 A * | 2/1975 | Honnen | .......................... 44/334 |
| 4,234,435 A | 11/1980 | Meinhardt et al. | |
| 5,234,612 A * | 8/1993 | Carlisle | ........................ 508/259 |
| 5,308,364 A * | 5/1994 | Gutierrez | ................ C10L 1/221 44/317 |
| 5,597,390 A * | 1/1997 | Loper | ................... C07C 229/16 44/391 |
| 6,599,335 B1 * | 7/2003 | Krull | ..................... C08F 210/00 44/386 |
| 7,214,649 B2 * | 5/2007 | Loper | ................. C10M 133/54 508/232 |
| 2005/0267003 A1 * | 12/2005 | Camenzind et al. | ......... 508/447 |

FOREIGN PATENT DOCUMENTS

| | | | |
|---|---|---|---|
| DE | 2054649 A1 | 5/1972 | |
| EP | 0061894 A2 | 10/1982 | |
| EP | 0286596 A2 | 10/1988 | |
| EP | 0336664 A2 | 10/1989 | |
| EP | 0 263 703 | 5/1991 | |
| EP | 1466959 A1 | 10/2004 | |
| EP | 1932899 A1 | 6/2008 | |
| GB | 960493 | 6/1964 | |
| WO | WO 2000/023541 A1 | 4/2000 | |
| WO | WO 0023541 A1 * | 4/2000 | |
| WO | WO 2002/062142 A1 | 8/2002 | |
| WO | WO 2004/026811 A2 | 4/2004 | |
| WO | WO 2007/147753 A2 | 12/2007 | |
| WO | WO 2007147753 A2 * | 12/2007 | |

OTHER PUBLICATIONS

Machine Translation of WO 0023541 A1.*
Machine Translation of WO 2007147753 A2.*
E. M. Landau et al., Stereochemical Studies in Crystal Nucleation, pp. 1436-1445, vol. 111, No. 4, J. Am. Chem. Soc. 1989.

* cited by examiner

*Primary Examiner* — Ellen M McAvoy
*Assistant Examiner* — Ming Cheung Po
(74) *Attorney, Agent, or Firm* — Orrick, Herrington & Sutcliffe LLP; Joseph A. Calvaruso

(57) ABSTRACT

A fuel oil composition comprising a major amount of a fuel oil and a minor amount of a compound being the product of the 1,4-addition reaction of (i) ammonia, a primary or secondary hydrocarbyl-substituted amine or a mixture thereof to (ii) a species containing one or more α,β-unsaturated carbonyl groups, wherein the compound includes at least one hydrocarbyl group containing at least 10 carbon atoms. The fuel oil composition has improved low temperature properties.

15 Claims, No Drawings

ADDITIVES FOR FUEL OILS

This invention relates to improved fuel oil compositions, more especially to fuel oil compositions susceptible to wax formation at low temperatures. The invention also relates to fuel oil compositions susceptible to wax formation at low temperatures which further include detergent additives.

Fuel oils, whether derived from petroleum or from vegetable sources, contain components, e.g., n-alkanes or methyl n-alkanoates, that at low temperature tend to precipitate as large, plate-like crystals or spherulites of wax in such a way as to form a gel structure which causes the fuel to lose its ability to flow. The lowest temperature at which the fuel will still flow is known as the pour point.

As the temperature of a fuel falls and approaches the pour point, difficulties arise in transporting the fuel through lines and pumps. Further, the wax crystals tend to plug fuel lines, screens, and filters at temperatures above the pour point. These problems are well recognised in the art, and various additives have been proposed, many of which are in commercial use, for depressing the pour point of fuel oils. Similarly, other additives have been proposed and are in commercial use for reducing the size and changing the shape of the wax crystals that do form. Smaller size crystals are desirable since they are less likely to clog a filter. The wax from a diesel fuel, which is primarily an alkane wax, crystallizes as platelets. Certain additives inhibit this and cause the wax to adopt an acicular habit, the resulting needles being more likely to pass through a filter, or form a porous layer of crystals on the filter, than are platelets. Other additives may also have the effect of retaining the wax crystals in suspension in the fuel, reducing settling and thus also assisting in prevention of blockages. These types of additives are often termed 'wax anti-settling additives' (WASA). Accordingly, WASAs typically lower the cold filter plugging point (CFPP) of a fuel (i.e. lower the temperature at which a fuel will cause a fuel filter to block) thereby permitting the fuel to flow more readily through a filter at a lower temperature.

Many additives have been described over the years for enhancing engine cleanliness, e.g. for reducing or removing deposits in the intake system (e.g. carburetors, intake manifold, inlet valves) or combustion chamber surfaces of spark-ignition engines, or for reducing or preventing injector nozzle fouling in compression-ignition engines.

For example, UK Patent specification No. 960,493 describes the incorporation of metal-free detergents, in the form of polyolefin-substituted succinimides of tetraethylene pentamine, in base fuels for internal combustion engines. The use of such metal-free detergents is now widespread. Most commonly used are polyisobutylene substituted succinimides which are the reaction products of polyisobutylene substituted acylating agents such as succinic acid or anhydride with polyamines. Such materials and their methods of production will be known to those skilled in the art.

The trend in modern diesel engine technology is to increase power output and efficiency by increasing injection pressures and decreasing injector nozzle diameters. Under these conditions, the build up of injector deposits is more likely and the deposition which occurs is more severe. This has led fuel manufacturers to produce new types of fuels which are often sold as 'premium' grades and promoted as being especially effective to improve engine cleanliness. To meet this performance claim, such premium fuels usually contain significantly higher levels of detergent than non-premium grade fuels.

Whilst largely effective with regard to engine cleanliness, a drawback has been identified with the use of high levels of detergent in fuel oils. Specifically, it has been observed that the presence of high levels of polyamine detergent species in premium grade fuels can interfere with the cold-flow performance of wax anti-settling additives when these are also present in the fuel. So, although the fuel may be satisfactory from an engine cleanliness viewpoint, its low temperature properties, in terms of wax anti-settling and cold filter plugging point (CFPP) may not be adequate.

The present invention is based on the discovery of a group of compounds which are effective as wax anti-settling additives in fuel oils. In addition, the compounds of the present invention are effective for lowering the CFPP temperature of a fuel oil. As well as providing fuel oils with improved low temperature properties, many of the compounds of the invention have the added advantage that their potency is much less affected by the presence of conventional fuel oil detergents.

Thus in accordance with a first aspect, the present invention provides a fuel oil composition comprising a major amount of a fuel oil and a minor amount of a compound being the product of the 1,4-addition reaction of (i) ammonia, a primary or secondary hydrocarbyl-substituted amine or a mixture thereof to (ii) a species containing one or more $\alpha,\beta$-unsaturated carbonyl groups, wherein the compound includes at least one hydrocarbyl group containing at least 10 carbon atoms and, optionally, the product of the 1,4-addition reaction of (i) to (ii) is further reacted with (iii) a hydrocarbyl compound containing one or more hydroxy, primary or secondary amino functional groups.

Preferably, the compound used includes at least one hydrocarbyl group, preferably an aliphatic hydrocarbyl group, such as an alkyl or alkylenyl group, containing from at least 12, preferably at least 14, more preferably at least 16 carbon atoms. Preferably, the compound includes at least one hydrocarbyl group, preferably an aliphatic hydrocarbyl group, such as an alkyl or alkylenyl group, containing up to 40, preferably up to 30, more preferably up to 24 carbon atoms.

Suitably, the compound used in the first aspect is a wax anti-settling additive for a fuel oil.

Suitably, the compound used in the first aspect lowers the CFPP temperature of a fuel oil.

Suitably, species (ii) may contain two or more $\alpha,\beta$-unsaturated carbonyl groups.

Preferably, species (ii) comprises an $\alpha,\beta$-unsaturated amide, an $\alpha,\beta$-unsaturated acid, an $\alpha,\beta$-unsaturated ester or an $\alpha,\beta$-unsaturated anhydride. More preferably, species (ii) comprises an acrylamide, a methacrylamide, acrylic acid, methacrylic acid, crotonoic acid, maleic acid, fumaric acid, an acrylic acid ester, a methacrylic acid ester, a crotonoic acid ester, a fumaric acid ester or a maleic acid ester.

The reaction between species (i) and species (ii) is facile and may be effected by simply heating the mixture of reactants for a given time. Temperatures of between 80 and 120° C., e.g. 100° C., have been found to be suitable. Reaction times of a few hours are generally adequate. Typically, the reaction is carried out in a suitable solvent, such as toluene or xylene. Typically, the reaction is performed in the presence a metallic Lewis acid catalyst to promote the 1,4-addition of species (i) to species (ii). Suitable catalysts include metallic chlorides, especially ferric chloride. As will be appreciated, the molar ratio of species (i) to species (ii) may be varied dependent on the type of amine (i) employed, the number of $\alpha,\beta$-unsaturated carbonyl groups present in species (ii) and the desirable predominant product of reaction. For example, 1 mole of a secondary hydrocarbyl-substituted amine may be reacted with 1 mole of species (ii) that contains one α,β-unsaturated carbonyl group to form predominantly the 1,4 addition product. Whereas, 1 mole of a primary hydrocarbyl-substituted amine may be reacted with 1 mole or an excess (i.e. 2 moles or more) of species (ii) that contains one α,β-unsaturated carbonyl group depending on whether the desirable product of reaction is the 1,4 addition product or it is desirable to further react the 1,4 addition product with a further species (ii).

In this specification, the following words and expressions, if and when used, have the meanings ascribed below:

"comprising" or any cognate word specifies the presence of stated features, steps, or integers or components, but does not preclude the presence or addition of one or more other features, steps, integers, components or groups thereof. The expressions "consists of" or "consists essentially of" or cognates may be embraced within "comprises" or cognates, wherein "consists essentially of" permits inclusion of substances not materially affecting the characteristics of the composition to which it applies;

"hydrocarbyl" means a chemical group of a compound that contains hydrogen and carbon atoms and that is bonded to the remainder of the compound directly via a carbon atom. The group may contain one or more atoms other than carbon and hydrogen provided they do not affect the essentially hydrocarbyl nature of the group. Preferably, the group consists essentially of hydrogen and carbon atoms, unless specified otherwise. Preferably, the hydrocarbyl group comprises an aliphatic hydrocarbyl group. The term "hydrocarbyl" includes "alkyl", "alkylene" and "alkylenyl" as defined herein;

"alkyl" means a $C_1$ to $C_{40}$ group which is bonded to the remainder of the compound directly via a single carbon atom. Unless otherwise specified, alkyl groups may, when there are a sufficient number of carbon atoms, be linear or branched, be cyclic, acyclic or part cyclic/acyclic. Preferably, the alkyl group comprises an acyclic alkyl group, more preferably a linear alkyl group. Representative examples of alkyl groups include, but are not limited to, methyl, ethyl, n-propyl, iso-propyl, n-butyl, sec-butyl, iso-butyl, tert-butyl, n-pentyl, iso-pentyl, neo-pentyl, hexyl, heptyl, octyl, dimethyl hexyl, nonyl, decyl, undecyl, dodecyl, tridecyl, tetradecyl, pentadecyl, hexadecyl, heptadecyl, octadecyl, nonadecyl, icosyl, triacontyl and tetracontyl. When specified, the alkyl group may be substituted or terminated by one or more substituents as defined herein, and/or be interrupted by one or more oxygen atoms and/or amino groups;

"alkylene" and "alkylenyl" means a $C_1$ to $C_{40}$ group which is bonded to the remainder of the compound directly via at least two carbon atoms and is otherwise defined in the same way as "alkyl". Preferably, the alkylenyl group comprises an acyclic alkylenyl group, more preferably a linear alkylenyl group. Representative examples of "alkylene" and "alkylenyl" include, but are not limited to, —$(CH_2)_n$— where n is 1 to 40, —$CH(CH_3)CH_2$—;

"active ingredients" or "(a.i.)" refers to additive material that is not diluent or solvent;

CFPP means cold flow plugging point as measured in accordance with ASTM D-6371-05.

It will be appreciated that species (ii) containing one or more α,β-unsaturated carbonyl groups contains an alkenyl group and cis (E) and trans (Z) isomerism may occur. Suitably, species (ii) as defined herein includes all the individual stereoisomers of species (ii) and, where appropriate, all individual tautomeric forms thereof; together with mixtures thereof.

Similarly, the compound used in the present invention includes all the individual stereoisomers and, where appropriate, all the individual tautomeric forms thereof, together with mixtures thereof.

The various features of the invention, which are applicable as appropriate to all aspects will now be described in more detail.

(i) The Amine

The amine of species (i) is selected from the group consisting of ammonia, a primary hydrocarbyl substituted amine, a secondary hydrocarbyl substituted amine, or a mixture thereof. The amine of species (i) may be represented by the formula $NHR^1R^2$, where $R^1$ and $R^2$ each independently represent hydrogen or a hydrocarbyl group which group is optionally terminated with one or more substituents selected from —OH or —$NH_2$ and/or interrupted by one or more oxygen atoms or —N(H)— groups.

When the amine of species (i) consists essentially of ammonia, then species (ii), as defined herein, containing one or more α,β-unsaturated carbonyl groups also includes at least one hydrocarbyl group, such as an alkyl or alkylenyl group, containing at least 10 carbon atoms, preferably containing from 10 to 40 carbon atoms. Consequently, the product of reaction includes a hydrocarbyl group containing at least 10 carbon atoms.

Preferably, the primary hydrocarbyl substituted amine and secondary hydrocarbyl substituted amine of species (i) may be represented by the formula $NHR^1R^2$, where $R^1$ independently represents a hydrocarbyl group, such as an alkyl group, containing from 10 to 40 carbon atoms which group is optionally terminated with an —$NH_2$ substituent and/or interrupted by one or more —N(H)— groups, and $R^2$ independently represents hydrogen or a hydrocarbyl group, such as an alkyl group, containing up to 40 carbon atoms which group is optionally terminated with an —$NH_2$ substituent and/or interrupted by one or more —N(H)— groups. More preferably, the primary hydrocarbyl substituted amine and secondary hydrocarbyl substituted amine of species (i) include amines where $R^1$ independently represents a hydrocarbyl group, such as an alkyl group, containing from 10 to 40 carbon atoms, and $R^2$ independently represents hydrogen or a hydrocarbyl group, such as an alkyl group, containing 10 to 40 carbon atoms. Most preferably, the primary hydrocarbyl substituted amine and secondary hydrocarbyl substituted amine of species (i) include amines where $R^1$ independently represents a hydrocarbyl group, such as an alkyl group, containing from 10 to 20 carbon atoms, and $R^2$ independently represents hydrogen or a hydrocarbyl group, such as an alkyl group, containing 10 to 20 carbon atoms Examples of primary amines include decylamine, dodecylamine, tetradecyl amine, hexadecylamine and octadecylamine. A preferred primary amine is octadecylamine.

Examples of secondary amines include dioctadecyl amine and dihexadecyl amine. Amine mixtures are suitable such as those derived from natural materials. A preferred secondary amine is a secondary hydrogenated tallow amine where $R^1$ and $R^2$ are alkyl groups derived from hydrogenated tallow fat composed of approximately 4% $C_{14}$, 31% $C_{16}$ and 59% $C_{18}$. Also preferred is cocoamine.

Highly preferred amines of species (i) include ammonia, octadecylamine and a secondary hydrogenated tallow amine where $R^1$ and $R^2$ are alkyl groups derived from hydrogenated tallow fat composed of approximately 4% $C_{14}$, 31% $C_{16}$ and 59% $C_{18}$.

(ii) The Species Containing One or More α,β-Unsaturated Carbonyl Groups

Preferably, the species (ii) containing one or more α,β-unsaturated carbonyl groups may be represented by a compound of general formula A-B wherein:

A comprises a moiety of general formula I which is bonded to B via the carbonyl group:

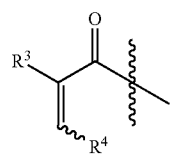

(I)

wherein:
$R^3$ and $R^4$ each independently represent hydrogen, $C_1$ to $C_8$ hydrocarbyl group, or —C(O)OR$^5$, where $R^5$ independently represents hydrogen or a hydrocarbyl group, such as an alkyl group, containing from 1 to 40 carbon atoms; and, B independently represents —NR$^6$R$^7$ or —OR$^8$ wherein:
$R^6$ and $R^7$ each independently represent hydrogen or a hydrocarbyl group, such as an alkyl group, containing up to 40 carbon atoms which group is optionally substituted or terminated with one or more substituents selected from —OR$^9$, —NR$^{10}$R$^{11}$, or a combination thereof, and/or interrupted by one or more oxygen atoms and/or —N(R$^{12}$)— groups, where $R^9$, $R^{10}$, $R^{11}$ and $R^{12}$ each independently represent hydrogen, a hydrocarbyl group containing up to 20 carbon atoms, or a moiety of general formula I as defined herein; and, $R^8$ independently represents hydrogen or a hydrocarbyl group, such as an alkyl group, containing up to 40 carbon atoms which group is optionally substituted or terminated with one or more substituents selected from —OR$^{13}$, —NR$^{14}$R$^{15}$, or a combination thereof, and/or interrupted by one or more oxygen atoms and/or —N(R$^{16}$)— groups, where $R^{13}$, $R^{14}$, $R^{15}$ and $R^{16}$ each independently represent hydrogen, a hydrocarbyl group containing up to 20 carbon atoms, or a moiety of general formula I as defined herein.

Preferably, $R^3$ independently represents hydrogen or a $C_1$ to $C_8$ hydrocarbyl group. More preferably, $R^3$ independently represents hydrogen or a $C_1$ to $C_8$ alkyl group. Most preferably, $R^3$ independently represents hydrogen or a methyl group, especially hydrogen.

Preferably, $R^4$ independently represents hydrogen, a $C_1$ to $C_8$ alkyl group or —C(O)OR$^5$, where $R^5$ independently represents hydrogen or a hydrocarbyl group, such as an alkyl group, containing from 1 to 24 carbon atoms. More preferably, $R^4$ independently represents hydrogen, a methyl group or —C(O)OR$^5$, where $R^5$ independently represents hydrogen or a hydrocarbyl group, such as an alkyl group, containing from 1 to 24 carbon atoms.

Preferably, $R^6$, when present, independently represents hydrogen or a hydrocarbyl group, such as an alkyl group, containing up to 40 carbon atoms. More preferably, $R^6$ independently represents hydrogen or an alkyl group, containing up to 20 carbon atoms.

Preferably, $R^7$, when present, independently represents hydrogen or a hydrocarbyl group, such as an alkyl group, containing up to 40 carbon atoms, more preferably up to 20 carbon atoms, which group is optionally substituted or terminated with one or more substituents selected from —OR$^9$ and/or —NR$^{10}$R$^{11}$, as defined herein, and/or interrupted by one or more —N(R$^{12}$)— groups as defined herein.

Preferably, $R^9$, when present, independently represents hydrogen, or an alkyl group, containing up to 20 carbon atoms, preferably containing up to 10 carbon atoms. Most preferably, $R^9$, when present, represents hydrogen.

Preferably, $R^{10}$, when present, independently represents hydrogen, or an alkyl group, containing up to 20 carbon atoms, preferably containing up to 10 carbon atoms. Most preferably, $R^{10}$, when present, represents hydrogen.

Preferably, $R^{11}$, when present, independently represents hydrogen, or an alkyl group, containing up to 20 carbon atoms, preferably containing up to 10 carbon atoms, or a moiety of general formula I as defined herein. Suitably, when $R^{11}$ represents a moiety of general formula I then the compound of general formula A-B includes two or more α,β-unsaturated carbonyl groups.

Preferably, $R^{12}$, when present, independently represents hydrogen, or an alkyl group, containing up to 20 carbon atoms, preferably containing up to 10 carbon atoms. Most preferably, $R^{12}$, when present, represents hydrogen.

Preferably, $R^8$, when present, independently represents hydrogen or a hydrocarbyl group, such as an alkyl group, containing up to 40 carbon atoms, more preferably up to 24 carbon atoms, which group is optionally substituted or terminated with one or more substituents selected from —OR$^{13}$ and/or —NR$^{14}$R$^{15}$, as defined herein, and/or interrupted by one or more oxygen atoms. More preferably, $R^8$, when present, independently represents hydrogen or a hydrocarbyl group, such as an alkyl group, containing up to 40 carbon atoms, more preferably up to 24 carbon atoms, which group is optionally substituted or terminated with one or more —OR$^{13}$ substituents, as defined herein, and/or interrupted by one or more oxygen atoms.

Preferably, $R^{13}$, when present, independently represents hydrogen, or an alkyl group, containing up to 20 carbon atoms, preferably containing up to 10 carbon atoms, or a moiety of general formula I as defined herein. Suitably, when $R^{13}$ represents a moiety of general formula I then the compound of general formula A-B includes two or more α,β-unsaturated carbonyl groups.

Preferably, $R^{14}$ and $R^{15}$, when present, each independently represent hydrogen or an alkyl group, containing up to 20 carbon atoms, preferably containing up to 10 carbon atoms.

Preferably, $R^{16}$, when present, independently represents hydrogen, or an alkyl group, containing up to 20 carbon atoms, preferably containing up to 10 carbon atoms. Most preferably, $R^{16}$, when present, represents hydrogen.

A preferred species (ii) is an α,β-unsaturated amide, such as an acrylamide or methacrylamide, and derivatives thereof, for example N-hydrocarbyl substituted and N,N dihydrocarbyl substituted acrylamides or methacrylamides. Such compounds may be represented by the general formula II

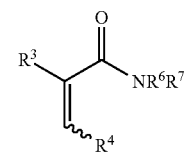

(II)

wherein $R^3$, $R^4$, $R^6$ and $R^7$ are as defined herein for a compound of general formula A-B. Preferred species (ii) of general formula II include compounds wherein:

$R^3$ is as defined for a compound of general formula A-B;

$R^4$ independently represents hydrogen or a $C_1$ to $C_8$ hydrocarbyl group. More preferably $R^4$ independently represents hydrogen or a $C_1$ to $C_8$ alkyl group. Most preferably, $R^4$ independently represents hydrogen or a methyl group, especially hydrogen; and, $R^6$ and $R^7$ both represent hydrogen, or $R^6$ represents hydrogen and $R^7$ represents a hydrocarbyl group, such as an alkyl group, containing up to 40 carbon atoms, more preferably up to 20 carbon atoms, or $R^6$ and $R^7$ both represent a hydrocarbyl group, such as an alkyl group, containing up to 40 carbon atoms, more preferably up to 20 carbon atoms, or $R^6$ represents hydrogen and $R^7$ represents a hydrocarbyl group, such as an alkyl group, containing up to 40 carbon atoms, more preferably up to 20 carbon atoms, which group is terminated by —$OR^9$, where $R^9$ is as defined herein for a compound of general formula A-B, or $R^6$ represents hydrogen and $R^7$ represents a hydrocarbyl group, such as an alkyl group, containing up to 40 carbon atoms, more preferably up to 20 carbon atoms, which group is terminated by —$NR^{10}R^{11}$, where $R^{10}$ is as defined herein for a compound of general formula A-B and $R^{11}$ is a moiety of general formula I as defined herein, or $R^6$ represents hydrogen and $R^7$ represents a hydrocarbyl group, such as an alkyl group, containing up to 40 carbon atoms, more preferably up to 20 carbon atoms, which group is terminated by —$NR^{10}R^{11}$, where $R^{10}$ is as defined herein for a compound of general formula A-B and $R^{11}$ independently represents hydrogen, or an alkyl group, containing up to 20 carbon atoms, preferably containing up to 10 carbon atoms, or $R^6$ represents hydrogen and $R^7$ represents a hydrocarbyl group, such as an alkyl group, containing up to 40 carbon atoms, more preferably up to 20 carbon atoms, which group is interrupted by one or more —$N(R^{12})$— groups and terminated by —$NR^{10}R^{11}$, where $R^{10}$ and $R^{12}$ are as defined herein for a compound of general formula A-B and $R^{11}$ is a moiety of general formula I as defined herein, or $R^6$ represents hydrogen and $R^7$ represents a hydrocarbyl group, such as an alkyl group, containing up to 40 carbon atoms, more preferably up to 20 carbon atoms, which group is interrupted by one or more —$N(R^{12})$— groups and is terminated by —$NR^{10}R^{11}$, where $R^{10}$ and $R^{12}$ are as defined herein for a compound of general formula A-B and $R^{11}$ independently represents hydrogen, or an alkyl group, containing up to 20 carbon atoms, preferably containing up to 10 carbon atoms.

Non-limiting examples include acrylamide, N-hydroxymethyl acrylamide, N,N dimethyl acrylamide, N,N'-methylenebis(acrylamide), N-(butoxymethyl)acrylamide, N-tert-butyl acrylamide and the corresponding (meth)acrylamides.

An alternative preferred species (ii) is an α,β-unsaturated acid, an α,β-unsaturated ester or an α,β-unsaturated anhydride, such as an acrylic acid, methacrylic acid, crotonoic acid, fumaric acid and maleic acid, and derivatives thereof, for example their ester and anhydride derivatives. Such compounds may be represented by the general formula III

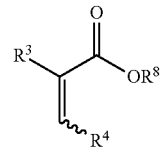

(III)

wherein $R^3$, $R^4$ and $R^8$ are as defined herein for a compound of general formula A-B. Preferred species (ii) of general formula II include compounds wherein:

$R^3$ and $R^4$ are as defined for a compound of general formula A-B; and, $R^8$ represents hydrogen, or $R^8$ represents a hydrocarbyl group, such as an alkyl group, containing up to 40 carbon atoms, more preferably up to 24 carbon atoms, or $R^8$ represents a hydrocarbyl group, such as an alkyl group, containing up to 40 carbon atoms, more preferably up to 24 carbon atoms, which group is terminated or substituted with one or more —$OR^{13}$ substituents where $R^{13}$ is a moiety of general formula I as defined herein, or $R^8$ represents a hydrocarbyl group, such as an alkyl group, containing up to 40 carbon atoms, more preferably up to 24 carbon atoms, which group is interrupted by one or more oxygen atoms and terminated or substituted with one or more —$OR^{13}$ substituents where $R^{13}$ is a moiety of general formula I as defined herein, or $R^8$ represents a hydrocarbyl group, such as an alkyl group, containing up to 40 carbon atoms, more preferably up to 24 carbon atoms, which group is terminated or substituted with one or more —$OR^{13}$ substituents where $R^{13}$ represents hydrogen, or $R^8$ represents a hydrocarbyl group, such as an alkyl group, containing up to 40 carbon atoms, more preferably up to 24 carbon atoms, which group is interrupted by one or more oxygen atoms and terminated or substituted with one or more —$OR^{13}$ substituents where $R^{13}$ represents hydrogen, or $R^8$ represents a hydrocarbyl group, such as an alkyl group, containing up to 40 carbon atoms, more preferably up to 24 carbon atoms, which group is terminated or substituted with one or more —$OR^{13}$ substituents where $R^{13}$ represents an alkyl group containing up to 20 carbon atoms, preferably containing up to 10 carbon atoms, or $R^8$ represents a hydrocarbyl group, such as an alkyl group, containing up to 40 carbon atoms, more preferably up to 24 carbon atoms, which group is interrupted by one or more oxygen atoms and terminated or substituted with one or more —$OR^{13}$ substituents where $R^{13}$ represents an alkyl group containing up to 20 carbon atoms, preferably containing up to 10 carbon atoms.

Non-limiting examples include acrylic acid, methacrylic acid, alkyl acrylates such as methyl acrylate, tert-butyl acrylate and octadecyl acrylate, alkyl methacrylates such as methyl methacrylate, tert-butyl methacrylate and octadecyl methacrylate, alkyl crotonoates such as methyl crotonoate and ethyl crotonoate, alkyl maleates such as dimethyl maleate, diethyl maleate and dioctadecyl maleate, hydroxylalkyl acrylates such as 2-hydroxyethyl acrylate and 3-hydroxypropyl acrylate, hydroxyalkyl methacrylates such as 2-hydroxyethyl methacrylate and 3-hydroxypropyl methacrylate, di- and tri-acrylates and methacrylates such as diethyleneglycol diacrylate, tripropyleneglycol diacrylate, 1,6-hexanediol diacrylate, polyethylene glycol diacrylate, bis-phenol A propoxylate diacrylate and trimethylolpropane triacrylate. Preferred examples include acrylic acid, methacrylic acid, alkyl acrylates, alkyl methacrylates, methyl crotonoate and trimethylolpropane triacrylate.

It will be appreciated that the amine species (i) as defined herein undergoes a 1,4 addition reaction with at least one of the one or more α,β-unsaturated carbonyl groups contained within species (ii). Suitably, if species (ii) contains a single α,β-unsaturated carbonyl group as defined herein, then the initial reaction product may be represented by general formula IV

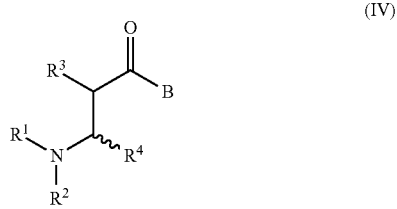

(IV)

wherein $R^1$, $R^2$, $R^3$, $R^4$ and B are as defined herein. If either of $R^1$ or $R^2$ in a compound of general formula IV represent hydrogen then it is possible for compound IV to undergo further 1,4 addition reactions with the at least one of the one or more α,β-unsaturated carbonyl groups contained within species (ii) Suitably, if B in a compound of species (ii) includes a further moiety of general formula I as defined herein (i.e. a further α,β-unsaturated carbonyl group), then the amine species (i) may also react with that α,β-unsaturated carbonyl group.

In a particularly preferred embodiment species (i) is a hydrocarbyl substituted di-amine or polyamine or an aminoalkanol and species (ii) is an α,β-unsaturated di-ester. Accordingly in another aspect, the present invention provides a compound being the product of the 1,4-addition reaction of (i) an amine represented by the formula $NHR^1R^2$, where $R^1$ and $R^2$ each independently represent hydrogen or a hydrocarbyl group which group is optionally terminated with one or more substituents selected from —OH or —$NH_2$ and/or interrupted by one or more oxygen atoms or —N(H)— groups to (ii) a species represented by the general formula III

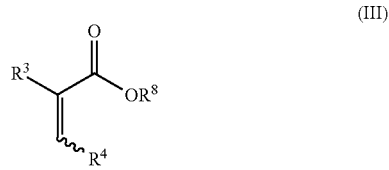

(III)

wherein $R^3$ represents hydrogen or a $C_1$ to $C_8$ hydrocarbyl group, wherein $R^4$ represents —$C(O)OR^5$, where $R^5$ and $R^8$ independently represent a hydrocarbyl group, such as an alkyl group, containing from 1 to 40 carbon atoms.

Preferably, species (i) is an amine represented by the formula $NHR^1R^2$, where $R^1$ represents hydrogen and $R^2$ represents a hydrocarbyl group which group is terminated with one or more substituents selected from —OH or —$NH_2$, preferably —$NH_2$.

Non-limiting examples of species (i) include alkanediamines such as 1,3-propanediamine, 1,4-butanediamine, 1,6-hexanediamine, 1,2-bis(3-aminopropylamino)ethane, 1,5-diamino-2-methylpentane, 3-(dimethylamino)propylamine, 3-(methylamino)propylamine, 3,3'-diamino-N-methyl-dipropylamine and aminoalkanols such as 3-aminopropanol. Non-limiting examples of species (ii) include di-alkyl maleates and di-alkyl fumarates such as di-octadecyl maleate, di-behenyl maleate and di-hexadecyl maleate. A particularly preferred compound is the product of the 1,4-addition reaction of 1 mole of 1,3-propanediamine to 2 moles of di-octadecyl maleate.

(iii) Further Reaction with Amines and Alcohols

The product resulting from the reaction of species (ii) with the amine species (i) may be further reacted with a species (iii), namely a hydrocarbyl compound which contains one or more hydroxy functional groups and/or one or more primary or secondary amino functional groups. Species (iii) may be represented by the general formula V

(V)

wherein $R^{17}$ represents a hydrocarbyl group, such as an alkyl or alkylenyl group, containing up to 40 carbon atoms which group is optionally substituted or terminated with one or more substituents selected from —OH, —$NR^{18}R^{19}$, or a combination thereof, and/or interrupted by one or more oxygen atoms and/or —$N(R^{20})$— groups, where $R^{18}$, $R^{19}$ and $R^{20}$ each independently represent hydrogen or a hydrocarbyl group containing up to 20 carbon atoms; and, X independently represents —OH or —$NHR^{21}$ wherein $R^{21}$ independently represents hydrogen or a hydrocarbyl group, such as an alkyl group, containing up to 40 carbon atoms which group is optionally substituted or terminated with one or more substituents selected from —OH, —$NR^{22}R^{23}$, or a combination thereof, and/or interrupted by one or more oxygen atoms and/or —$N(R^{24})$— groups, where $R^{22}$, $R^{23}$ and $R^{24}$ each independently represent hydrogen or a hydrocarbyl group containing up to 20 carbon atoms.

Preferred compounds of general formula (V) include those:

wherein $R^{17}$ represents a hydrocarbyl group, such as an alkyl group, containing up to 40 carbon atoms, preferably containing up to 20 carbon atoms, which group is optionally substituted or terminated with one or more substituents selected from —OH, —$NH_2$, or a combination thereof, and/or interrupted by one or more oxygen atoms and/or —N(H)— groups; and, X independently represents —OH or —$NHR^{21}$ wherein $R^{21}$ independently represents hydrogen or a hydrocarbyl group, such as an alkyl group, containing up to 40 carbon atoms, preferably containing up to 20 carbon atoms, which group is optionally substituted or terminated with one or more substituents selected from —OH, —$NH_2$, or a combination thereof, and/or interrupted by one or more oxygen atoms and/or —N(H)— groups.

Non-limiting examples of the compounds of general formula V include: mono-alcohols such as ethanol, propanol, butanol, pentanol, octanol, hexanol, dodecanol, hexadecanol, octadecanol; diols such as diethylene glycol, tripropylene glycol, ethylene glycol, propylene glycol; triols such as glycerol and trimethylolpropane; primary amines such as ethyl amine, propyl amine, octadecyl amine, 3-(dimethylamino)1-propylamine; di-, tri- and tetra-amines such as ethylene diamine, hexamethylene diamine, diaminobutane, putrescine, spermine and spermidine; amino alcohols such as ethanol amine, diethanol amine, N-ethyl ethanol amine, 2-(aminoethyl)aminoethanol, 2-(aminoethoxy)ethanol.

Conveniently, the reaction of species (iii) with the reaction product of species (i) and (ii) is facile. Typically, the reaction is preformed in a suitable solvent, such as toluene or xylene, at an elevated temperature e.g. 80 to 120° C. for a few hours in the presence of a basic catalyst, for example sodium methoxide or sodium ethoxide.

Suitably, species (iii), namely the hydrocarbyl compound which contains one or more hydroxy functional groups and/or one or more primary or secondary amino functional groups, may react with one or more functional groups which may be present in the reaction product of species (i) and species (ii). Such functional groups may include an ester functional group, for example derivable from a compound of general formula III, or an unreacted α,β-unsaturated carbonyl group, for example derivable from a compound A-B where B includes at least one α,β-unsaturated carbonyl group. Preferably, species (iii) is reacted with the reaction product of species (i) and species (ii), wherein species (ii) comprises a compound as represented by general formula III.

In accordance with a second aspect, the present invention provides an additive composition comprising a compound as defined in relation to the first aspect and a compatible solvent therefor.

In accordance with a third aspect, the present invention provides the use of a compound as defined in relation to the first aspect to improve the low temperature properties of a fuel oil composition.

A discussed above, some of compounds of the present invention have the additional advantage that they do not lose potency when used in combination with conventional fuel oil detergents. Thus in preferred embodiments, the fuel oil composition of the second aspect and the additive composition of the third aspect further comprise a fuel oil detergent.

In accordance with a fourth aspect, the present invention provides the use of a combination of a fuel oil detergent and a compound effective as a wax anti-settling additive to improve the detergency properties and low temperature properties of a fuel oil composition, wherein the low temperature properties of the fuel oil composition are at least substantially similar to the low temperature characteristics of the fuel oil composition comprising the compound effective as a wax anti-settling additive in the absence of the fuel oil detergent, the use comprising employing as the compound effective as a wax anti-settling additive, a compound according to the first aspect.

The term 'at least substantially similar' in the context of this fourth aspect should be understood to mean that the presence of the detergent does not have a significant negative influence on at least one of the low temperature characteristics (e.g. CFPP or wax anti-settling) of the fuel oil containing the compound of the invention compared to the situation where the detergent is absent. It is not required that the low temperature characteristics are improved in absolute terms merely that they are not adversely affected on a practical level. Of course, an improvement in absolute terms is also within the scope of the present invention.

Preferably, the fuel oil detergent comprises a polyamine detergent. A preferred class of polyamine detergents is those made by reacting an acylating agent having a hydrocarbyl substituent of at least 10 carbon atoms and a nitrogen compound characterized by the presence of at least one —NH— group. Typically, the acylating agent will be a mono- or polycarboxylic acid (or reactive equivalent thereof) such as a substituted succinic or propionic acid and the amino compound will be a polyamine or mixture of polyamines, most typically, a mixture of ethylene polyamines. The amine also may be a hydroxyalkyl-substituted polyamine. The hydrocarbyl substituent in such acylating agents preferably averages at least about 30 or 50 and up to about 200 carbon atoms.

Many patents have described suitable polyamine detergents including U.S. Pat. Nos. 3,172,892; 3,219,666; 3,272, 746; 3,310,492; 3,341,542; 3,444,170; 3,455,831; 3,455, 832; 3,576,743; 3,630,904; 3,632,511; 3,804,763 and 4,234, 435, and including European patent applications EP 0 336 664 and EP 0 263 703. A typical and preferred compound of this class is that made by reacting a poly(isobutylene)-substituted succinic anhydride acylating agent (e.g. anhydride, acid, ester, etc.) wherein the poly(isobutene) substituent has between about 50 to about 200 carbon atoms with a mixture of ethylene polyamines having 3 to about 10 amino nitrogen atoms per ethylene polyamine and about 1 to about 6 ethylene groups.

The polyamine component may be defined by the average number of nitrogen atoms per molecule of the component, which may preferably be in the range of 4 to 8.5, more preferably 6,8 to 8, especially 6.8 to 7.5 nitrogens per molecule.

A preferred polyamine detergent comprises the reaction product between a poly(isobutene) substituted succinic anhydride acylating agent with a polyamine or mixture of polyamines as hereinbefore described. Preferably, the poly (isobutene) has a number average molecular weight (Mn) of about 400-2500, preferably 400-1300, such as about 950.

The Fuel Oil

The fuel oil may be, e.g., a petroleum-based fuel oil, especially a middle distillate fuel oil. Such distillate fuel oils generally boil within the range of from 110° C. to 500° C., e.g. 150° C. to 400° C.

The invention is applicable to middle distillate fuel oils of all types, including the broad-boiling distillates, i.e., those having a 90%-20% boiling temperature difference, as measured in accordance with ASTM D-86, of 50° C. or more.

The fuel oil may comprise atmospheric distillate or vacuum distillate, cracked gas oil, or a blend in any proportion of straight run and thermally and/or catalytically cracked distillates. The most common petroleum distillate fuels are kerosene, jet fuels, diesel fuels, heating oils and heavy fuel oils. The heating oil may be a straight atmospheric distillate, or may also contain vacuum gas oil or cracked gas oil or both. The fuels may also contain major or minor amounts of components derived from the Fischer-Tropsch process. Fischer-Tropsch fuels, also known as FT fuels, include those that are described as gas-to-liquid fuels, coal and/or biomass conversion fuels. To make such fuels, syngas ($CO+H_2$) is first generated and then converted to normal paraffins and olefins by a Fischer-Tropsch process. The normal paraffins may then be modified by processes such as catalytic cracking/reforming or isomerisation, hydrocracking and hydroisomerisation to yield a variety of hydrocarbons such as iso-paraffins, cyclo-paraffins and aromatic compounds. The resulting FT fuel can be used as such or in combination with other fuel components and fuel types such as those mentioned in this specification. The above mentioned low temperature flow problem is most usually encountered with diesel fuels and with heating oils. The invention is also applicable to fuel oils containing fatty acid methyl esters derived from vegetable oils, for example, rapeseed methyl ester, soya-oil methyl ester, palm-oil methyl ester and the like, either used alone or in admixture with a petroleum distillate oil.

In an embodiment of all aspects of the present invention, the fuel oil comprises at least 2%, preferably at least 5% by weight of fatty acid methyl esters derived from vegetable oils.

The fuel oil is preferably a low sulphur content fuel oil. Typically, the sulphur content of the fuel oil will be less than 500 ppm (parts per million by weight). Preferably, the sulphur content of the fuel will be less than 100 ppm, for example, less than 50 ppm. Fuel oils with even lower sulphur contents, for example less that 20 ppm or less than 10 ppm are also suitable.

Treat Rates

The amounts of each component present in the fuel oil will depend on the nature of the species used, the properties of the fuel oil and the low temperature performance required.

The amount of compound (a.i.) according to the invention will typically be in the range of 10-500 ppm, preferably 10-200 ppm by weight based on the weight of the fuel oil.

When present, typically, the amount of fuel oil detergent (a.i.) in the fuel oil composition will be in excess of 50 ppm by weight based on the weight of the fuel oil, for example in excess of 75 ppm by weight or 100 ppm by weight. Some premium diesel fuels may contain up to 500 ppm by weight of polyamine detergent. This can be compared to a treat rate of around 10-75 ppm for non-premium diesel fuels.

Other Additives

It is commonplace in the art to use compounds effective as a wax anti-settling additives in combination with other additional cold-flow improving additives. Suitable materials will be well known to those skilled in the art and include for example, ethylene-unsaturated ester copolymers such as ethylene-vinyl acetate copolymers, comb polymers such as fumarate-vinyl acetate copolymers, hydrocarbon polymers such as hydrogenated polybutadiene polymers, ethylene/1-alkene copolymers, and similar polymers.

Also suitable are condensate species such as alkyl-phenol formaldehyde condensates as described in EP 0 857 776 B1, or hydroxy-benzoate formaldehyde condensates as described in EP-A-1 482 024.

The present invention contemplates the addition of such additional cold-flow improving additives; their application in terms of treat rate being also well known to those skilled in the art. In an embodiment of all aspects of the invention, the fuel oil further comprises one or more of an ethylene-unsaturated ester copolymer, a fumarate-vinyl acetate copolymer, an alkyl-phenol formaldehyde condensate, a hydroxy-benzoate formaldehyde condensate and a hydrocarbon polymer.

Evaluation of Low Temperature Properties.

As is known in the art, there are a number of methods which can be used to determine the low temperature properties of a fuel oil. Preferably, the low temperature properties are as determined by measuring the wax anti settling performance, CFPP, or both. The wax anti-settling performance can be measured using the ARAL Short sedimentation Test which measures $\Delta CP$. Preferably, the low temperature properties improved in the present invention are $\Delta CP$, CFPP or both.

$\Delta CP$ is a measurement of the propensity of the wax content of a fuel oil to settle and thus a determination of the effectiveness of a wax anti-settling additive. To determine $\Delta CP$, the cloud point (CP) of a base fuel oil is measured. The wax anti-settling additive under study is then added to the base fuel and the sample cooled to a temperature below the measured CP. This temperature may vary, in Germany a temperature of $-13°$ C. is commonly used, in South Korea it may be $-15$ or $-20°$ C. and a value of $-18°$ C. is also often used. After leaving the fuel oil sample for a time to allow any wax to settle, the CP of the bottom 20% by volume of the sample is measured. The difference between this measurement and the value obtained for the base fuel is $\Delta CP$. A small value, preferably around zero, of $\Delta CP$ indicates good wax dispersancy.

CFPP is a standard industry test to evaluate the ability of a fuel oil sample to flow through a filter at reduced temperature and it is measured in accordance with ASTM D-6371-05.

The invention will now be described by way of the following non-limiting examples.

Compounds were made as detailed in Table 1 below. Unless stated otherwise in Table 1, the compounds were prepared by reacting 1 mole of the amine for each mole of species (ii) containing the one or more $\alpha,\beta$-unsaturated carbonyl groups. The reactants were mixed in a suitable solvent, such as toluene, and heated to 100° C. for up to 7 hours. An iron (III) chloride ($1.5\times10^{-3}$ mol) catalyst was also employed, unless otherwise indicated. The progress of the reaction was monitored by thin layer chromatography and, upon completion, solids were removed by filtration and the filtrate evaporated to yield the desired product. The product, where necessary, was purified by known techniques and characterised by standard techniques, such as NMR.

TABLE 1

| No. | (i) Amine species | (ii) $\alpha,\beta$-unsaturated carbonyl group species |
|---|---|---|
| 1 | di-hydrogenated tallow amine | N-(hydroxymethyl)acrylamide |
| 2 | di-hydrogenated tallow amine | acrylamide |
| 3 | di-hydrogenated tallow amine | N,N'-methylenebis(acrylamide) |
| 4 | di-hydrogenated tallow amine | N,N-dimethylacrylamide |
| 5 | di-hydrogenated tallow amine (2 mol) | acrylic acid (1 mol) |
| 6 | octadecylamine | methyl methacrylate |
| 7 | di-hydrogenated tallow amine | acrylic acid |
| 8 | octadecylamine | methyl crotonoate |
| 9 | octadecylamine | dimethyl maleate* |
| 10 | di-hydrogenated tallow amine | methyl acrylate |
| 11 | octadecylamine (1 mol) | octadecyl acrylate (2 mol) |
| 12 | octadecylamine | octadecyl acrylate* |
| 13 | di-hydrogenated tallow amine (2 mol) | Diethylene glycol diacrylate (1 mol) |
| 14 | di-hydrogenated tallow amine (2 mol) | tripropylene glycol diacrylate (1 mol) |
| 15 | di-hydrogenated tallow amine | methyl crotonoate |
| 16 | di-hydrogenated tallow amine | 2-hydroxyethyl acrylate |
| 17 | di-hydrogenated tallow amine (2 mol) | trimethyolpropane triacrylate (1 mol) |
| 18 | di-hydrogenated tallow amine | t-butyl acrylate |
| 19 | di-hydrogenated tallow amine | octadecyl acrylate |

TABLE 1-continued

| No. | (i) Amine species | (ii) α,β-unsaturated carbonyl group species |
|---|---|---|
| 20 | di-hydrogenated tallow amine (2 mol) | bis-phenol A propoxylate diacrylate (1 mol) |
| 21 | di-hydrogenated tallow amine (3 mol) | trimethylolpropane triacrylate (1 mol) |
| 22 | di-hydrogenated tallow amine | N-t-butyl acrylamide |
| 23 | di-hydrogenated tallow amine | N-(butoxymethyl)acrylamide |
| 24 | ammonia (1 mol) | behenyl acrylate (2 mol)* |
| 25 | di-hydrogenated tallow amine | 1,6-hexanediol diacrylate |
| 26 | octadecylamine (2 mol) | 1,6-hexanediol diacrylate (1 mol)* |
| 27 | octadecylamine | 2-hydroxyethyl acrylate* |
| 28 | octadecylamine (2 mol) | acrylic acid (1 mol)* |
| 29 | octadecylamine (1 mol) | methyl acrylate (2 mol) |
| 30 | octadecylamine (2 mol) | PEG diacrylate 575 (1 mol)* |
| 31 | octadecylamine (3 mol) | tripropyleneglycol diacrylate (1 mol)* |
| 32 | ammonia (1 mol) | octadecyl acrylate (2 mol)* |
| 33 | ethylenediamine (1 mol) | octadecyl acrylate (2 mol)* |
| 34 | compound 33 | 1,6-hexanediol diacrylate |
| 35 | 1,3 propane diamine (1 mol) | di-octadecyl maleate (2 mol)* |
| 36 | 1,2-bis(3-aminopropylamino)ethane (1 mole | di-octadecyl maleate (2 mol) |
| 37 | 1,3 propane diamine (1 mol) | di-behenyl maleate (2 mol) |
| 38 | 1,4 butanediamine (1 mol) | di-octadecyl maleate (2 mol) |
| 39 | 1,5 diamino-2-methylpentane (1 mol) | di-octadecyl maleate (2 mol) |
| 40 | 1,6 hexanediamine (1 mol) | di-octadecyl maleate (2 mol) |
| 41 | 3-(dimethylamino)propylamine | di-behenyl maleate |
| 42 | 3-(dimethylamino)propylamine | di-hexadecyl maleate |
| 43 | 3-(methylamino)propylamine | di-octadecyl maleate |
| 44 | 3,3'-diamino-N-methyl-dipropylamine (1 mol) | di-octadecyl maleate (2 mol) |
| 45 | 3-aminopropanol | di-behenyl maleate |
| 46 | 3-aminopropanol | di-octadecyl maleate |
| 47 | bis(3-aminopropyl)amine (1 mol) | di-octadecyl maleate (2 mol) |
| 48 | m-xylenediamine (1 mol) | di-octadecyl maleate (2 mol) |

*Indicates no ferric chloride added

Compounds no. 9, 10, 24 or 34 as indicated in Table 1 above was further reacted with species (iii) a hydrocarbyl compound containing one or more amino and/or hydroxyl functional groups as detailed in Table 2 below. Unless stated otherwise in Table 2, the compounds were prepared by reacting 1 mole of Compound no. 10 for each mole of species (iii). The reactants were mixed in a suitable solvent, such as xylene, and heated to 100° C. for up to 8 hours. A base, such as sodium methoxide (0.1 mol) was also included. The progress of the reaction was monitored by thin layer chromatography and, upon completion, solids were removed by filtration and the filtrate evaporated to yield the desired product. The product, where necessary, was purified by known techniques and characterised by standard techniques, such as NMR.

TABLE 2

| No. | Compound of Table 1 | (iii) amino and/or hydroxyl species |
|---|---|---|
| 49 | 10 | 2-(aminoethyl)aminoethanol |
| 50 | 10 | 3-(dimethylamino-1-propylamine |
| 51 | 10 | N-ethylethanolamine |
| 52 | 10 (2 mol) | diethanolamine (1 mol) |
| 53 | 10 (2 mol) | ethanolamine (1 mol) |
| 54 | 10 | 2-(aminoethyl)aminoethanol |
| 55 | 10 | 3-amino propanol |
| 56 | 10 (3 mol) | triethanolamine (1 mol) |
| 57 | 10 (2 mol) | ethylene glycol (1 mol) |
| 58 | 10 | hydroxyethylethylene diamine |
| 59 | 10 | n-butyl amine |
| 60 | 10 | octadecyl amine |
| 61 | 10 (2 mol) | xylene diamine (1 mol) |
| 62 | 9 | 1,4-butanediol |
| 63 | 24 (2 mol) | phthalic anhydride (1 mol) |
| 64 | 34 (2 mol) | phthalic anhydride (1 mol) |

Table 3 below details the results of testing of compounds according to the present invention for both CFPP and ΔCP. The fuel used was low sulphur-content diesel fuel containing with a CP of −8.0° C. The diesel fuel portion had an initial boiling point of 203° C. and a final boiling point of 349° C. Each compound was used in an amount of 67 ppm by weight (a.i.) based on the weight of the fuel. Also added in each case was 433 ppm of a conventional middle distillate flow improver package being the combination of a mixture of ethylene vinyl acetate copolymers, a comb polymer, a phenolic formaldehyde condensate and a hydrogenated diblock copolymer of butadiene.

TABLE 3

| Compound | CFPP (° C.) | ΔCP (° C.) |
|---|---|---|
| none | −20.0 | 9.9 |
| 1 | −27.5 | 1.0 |
| 2 | −23.8 | 1.7 |
| 3 | −22.5 | 1.6 |
| 4 | −23.1 | 2.0 |
| 5 | −26.0 | 2.0 |
| 6 | −23.7 | 1.9 |
| 7 | −25.5 | 1.8 |
| 8 | −25.0 | 1.5 |
| 9 | −23.5 | 1.8 |
| 10 | −25.0 | 2.6 |
| 11 | −24.8 | 1.7 |
| 12 | −24.0 | 2.1 |
| 13 | −23.8 | 2.5 |
| 14 | −23.5 | 2.8 |
| 15 | −21.8 | 2.0 |
| 16 | −22.3 | 2.4 |
| 17 | −24.5 | 1.3 |
| 18 | −22.0 | 3.1 |
| 19 | −21.5 | 2.4 |
| 20 | −21.3 | 2.8 |
| 21 | −21.0 | 2.4 |

TABLE 3-continued

| Compound | CFPP (° C.) | ΔCP (° C.) |
|---|---|---|
| 22 | −26.0 | 1.1 |
| 23 | −25.0 | 1.3 |
| 24 | −23.5 | 1.7 |
| 25 | −23.3 | 1.1 |
| 26 | −21.0 | 1.3 |
| 27 | −25.5 | 1.1 |
| 28 | −21.0 | 1.5 |
| 29 | −22.5 | 1.4 |
| 30 | −21.0 | 1.9 |
| 31 | −22.0 | 1.3 |
| 32 | −22.0 | 2.3 |
| 34 | −21.0 | 1.4 |
| 35 | −25.0 | 0 |
| 49 | −24.8 | 1.3 |
| 50 | −23.2 | 2.3 |
| 51 | −22.7 | 1.9 |
| 52 | −22.3 | 2.4 |
| 53 | −21.0 | 2.0 |
| 55 | −22.3 | 1.9 |
| 56 | −21.3 | 1.7 |
| 57 | −25.0 | 1.3 |
| 58 | −23.9 | 2.1 |
| 59 | −22.3 | 2.3 |
| 60 | −21.0 | 2.0 |
| 61 | −22.0 | 2.3 |
| 62 | −25.8 | 1.1 |
| 63 | −26.0 | 1.2 |
| 64 | −23.5 | 1.5 |

Additional results are given in Table 4 below. Here the fuel used was a low sulphur-content diesel fuel containing 5% of FAME and having a cloud point of −7.0° C. The diesel fuel portion had an initial boiling point of 195° C. and a final boiling point of 350° C. Each compound was used in an amount of 50 ppm by weight based on the weight of the fuel. Also added in each case was 413 ppm by weight of a conventional middle distillate flow improver package being the combination of a mixture of ethylene vinyl acetate copolymers, a comb polymer and a phenolic formaldehyde condensate.

TABLE 4

| Compound | CFPP (° C.) | ΔCP (° C.) |
|---|---|---|
| none | −19.5 | 5.3 |
| 35 | −25.0 | −0.4 |
| 36 | −25.0 | 0.0 |
| 37 | −26.0 | 1.8 |
| 38 | −25.0 | −0.2 |
| 39 | −26.0 | −0.1 |
| 40 | −26.0 | 1.2 |
| 41 | −22.5 | 0.2 |
| 42 | −25.0 | 3.5 |
| 43 | −23.5 | 0.2 |
| 44 | −25.5 | −0.4 |
| 45 | −23.0 | 0.5 |
| 46 | −26.0 | 1.5 |
| 47 | −22.0 | −0.2 |
| 48 | −25.5 | 0.5 |

Table 5 below details the results of testing of compounds according to the present invention for ΔCP and the effect of the addition to the fuel of 100 ppm by weight (a.i.) of a conventional diesel fuel detergent being a polyisobutylene-substituted succinimide where the polyisobutylene substituent was of ca. 950 molecular weight and the amine was a mixture of polyethylene polyamines having an average of 6-8 nitrogen atoms per molecule. The fuel used was a low sulphur-content diesel fuel containing 5% by weight of soya oil methyl ester, with a CP of −7.0° C. The diesel fuel portion had an initial boiling point of 195° C. and a final boiling point of 350° C. Each compound was used in an amount of 75 ppm by weight (a.i.) based on the weight of the fuel. Also added in each case was 375 ppm of a conventional middle distillate flow improver package being the combination of a mixture of ethylene vinyl acetate copolymers, a comb polymer, a phenolic formaldehyde condensate and a hydrogenated diblock copolymer of butadiene. The table also provides results for a "Reference WASA" in the presence of detergent and in the absence of detergent. This was a product not according to the present invention being formed by the reaction of phthalic anhydride with di-hydrogenated tallow amine. It was tested in the same manner as the compounds of the invention.

TABLE 5

| Compound | ΔCP |
|---|---|
| 5 | 4.8 |
| 7 | 0.0 |
| 8 | 0.1 |
| 9 | 1.9 |
| 21 | 0.7 |
| 22 | 0.4 |
| 23 | 1.5 |
| 24 | 3.5 |
| 25 | 1.3 |
| 31 | −0.1 |
| 35 | 1.6 |
| Reference WASA | 8.3 |
| Reference WASA and no detergent | 0.0 |

The data obtained show that the compounds of the invention are effective to improve the low temperature properties of the fuel. Both good CFPP and ΔCP values were obtained and in all cases both of these values were improved compared to the fuel treated with the conventional middle distillate flow improver alone (Table 3).

In the majority of cases, the addition of the conventional detergent (Table 5) did not have a detrimental effect on the potency of the compounds. The Reference WASA performed poorly, losing a significant amount of ΔCP performance when the detergent was added.

What is claimed is:

1. A fuel oil composition comprising (a) a major amount of a fuel oil; and (b) 10-500 ppm by weight based on the weight of the fuel oil of a compound being the product of the 1,4-addition reaction of (i) ammonia, a primary or secondary hydrocarbyl-substituted amine or a mixture thereof to (ii) a species containing one or more α,β-unsaturated carbonyl groups, wherein the compound includes at least one hydrocarbyl group containing at least 10 carbon atoms; and
wherein species (ii) is of formula A-B,
wherein A comprises a moiety of general formula I which is bonded to B via the carbonyl group:

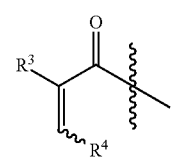

(I)

wherein $R^3$ represents hydrogen, $C_1$ to $C_8$ hydrocarbyl group, or $C(O)OR^5$, wherein $R^4$ represents $C_1$ to $C_8$ hydrocarbyl group, or —C(O)$OR^5$, where $R^5$ represents a hydrocarbyl group, containing from 1 to 40 carbon atoms, wherein B independently represents —$NR^6R^7$ or —$OR^8$, wherein $R^6$ and $R^7$ each independently represent hydrogen or a hydrocarbyl group, containing up to 40 carbon atoms which group is optionally substituted or terminated with one or more substituents selected from —$OR^9$, —$NR^{10}R^{11}$, or a combination thereof, and/or interrupted by one or more oxygen atoms and/or —N($R^{12}$)— groups, where $R^9$, $R^{10}$, $R^{11}$ and $R^{12}$ each independently represent hydrogen, a hydrocarbyl group containing up to 20 carbon atoms, or a moiety of general formula I; and, wherein $R^8$ independently represents hydrogen or a hydrocarbyl group, containing up to 40 carbon atoms which group is optionally substituted or terminated with one or more substituents of —$NR^{14}R^{15}$, and/or interrupted by one or more —N($R^{16}$)— groups, where $R^{14}$, $R^{15}$ and $R^{16}$ each independently represent hydrogen, a hydrocarbyl group containing up to 20 carbon atoms, or a moiety of general formula I as defined herein.

2. The fuel oil composition according to claim 1 wherein species (ii) comprises an α,β-unsaturated amide or, an α,β-unsaturated ester.

3. The fuel oil composition according to claim 2 wherein species (ii) comprises an acrylamide, a methacrylamide, an acrylic acid ester, a methacrylic acid ester, a crotonoic acid ester, a fumaric acid ester or a maleic acid ester.

4. The fuel oil composition according to claim 1 wherein species (ii) contains two or more α,β-unsaturated carbonyl groups.

5. The fuel oil composition according to claim 1 wherein (i) is of the formula $NHR^1R^2$, where $R^1$ independently represents a hydrocarbyl group containing from 8 to 40 carbon atoms, and $R^2$ independently represents hydrogen or a hydrocarbyl group containing up to 40 carbon atoms.

6. The fuel oil composition wherein the compound according to claim 1 is reacted with (iii) a hydrocarbyl compound containing one or more hydroxy, primary or secondary amino functional groups.

7. The fuel oil composition according to claim 1 further comprising one or more of an ethylene-unsaturated ester copolymer, a comb polymer, an alkyl-phenol formaldehyde condensate, a hydroxy-benzoate formaldehyde condensate and a hydrocarbon polymer.

8. An additive composition comprising a compound as defined in claim 1 and a compatible solvent therefor.

9. The fuel oil composition according to claim 1 further comprising a fuel oil detergent.

10. The fuel oil composition according to claim 1 wherein $R^5$ represents an alkyl group.

11. The fuel oil composition according to claim 1 wherein $R^6$ and $R^7$ each independently represent hydrogen or an alkyl group.

12. The fuel oil composition according to claim 1 wherein $R^8$ independently represents hydrogen or an alkyl group.

13. The fuel oil composition according to claim 5 wherein $R^1$ independently represents an alkyl group.

14. The fuel oil composition according to claim 5 wherein $R^2$ independently represents hydrogen or an alkyl group.

15. A fuel oil composition comprising (a) a major amount of a fuel oil; and (b) 10-500 ppm by weight based on the weight of the fuel oil of a compound being the product of the 1,4-addition reaction of (i) an amine represented by the formula $NHR^1R^2$, where $R^1$ and $R^2$ each independently represent hydrogen or a hydrocarbyl group which group is optionally terminated with one or more substituents selected from —OH or —$NH_2$ and/or interrupted by one or more oxygen atoms or —N(H)— groups to (ii) a species represented by general formula III

(III)

wherein $R^3$ represents hydrogen or a $C_1$ to $C_8$ hydrocarbyl group, wherein $R^4$ represents —C(O)$OR^5$, where $R^5$ and $R^8$ independently represent a hydrocarbyl group containing from 1 to 40 carbon atoms.

* * * * *